(12) United States Patent
Bishop (10) Patent No.: US 7,409,240 B1
(45) Date of Patent: Aug. 5, 2008

(54) SYSTEM AND METHOD FOR IMAGING MYOCARDIAL INFARCTION

(76) Inventor: Harry A. Bishop, 147 W. Main St., Suite 5, Bridgeport, WV (US) 26330

( * ) Notice: Subject to any disclaimer, the term of this patent is extended or adjusted under 35 U.S.C. 154(b) by 0 days.

(21) Appl. No.: 11/054,278

(22) Filed: Feb. 9, 2005

Related U.S. Application Data (60) Provisional application No. 60/543,438, filed on Feb. 9, 2004.

(51) Int. Cl.
*A61B 6/00* (2006.01)

(52) U.S. Cl. .................. 600/436; 600/407; 600/431

(58) Field of Classification Search ......... 600/407–437; 250/363.1, 370.09
See application file for complete search history.

(56) References Cited

U.S. PATENT DOCUMENTS 5,377,681 A * 1/1995 Drane ................... 600/419
5,431,161 A * 7/1995 Ryals et al. ............ 600/425

* cited by examiner

*Primary Examiner*—Brian L. Casler
*Assistant Examiner*—John F Ramirez
(74) *Attorney, Agent, or Firm*—Thompson Hine LLP (57) ABSTRACT

One aspect of the present invention relates to imaging a patient to determine whether he or she has suffered a myocardial infarction. According to this method, a patient is injected with a bolus having a radioactive tracer. A representative cycle is produced for both the right ventricular passage of the bolus and the left ventricular passage of the bolus based on planar coordinates over time of scintillation events of the tracer. A time activity curve based on activity in each segment of the respective representative cycles is generated. When a segment of heart muscle is damaged its contraction ceases or lags behind the normal surrounding myocardium resulting in a phase shift in the adjacent blood pool.

20 Claims, 9 Drawing Sheets

BOTTOM VIEW

Figure 4

SIDE VIEW

SYSTEM AND METHOD FOR IMAGING MYOCARDIAL INFARCTION

CROSS REFERENCE TO RELATED APPLICATIONS

This invention claims priority to U.S. Patent Application No. 60/543,438 filed Feb. 9, 2004.

FIELD OF INVENTION

The present invention relates to medical diagnostic and screening systems and methods. In particular, the present invention relates to non-invasive cardiac imaging and functional analysis systems and methods.

BACKGROUND OF INVENTION

While cardiac imaging and functional analysis is the largest single nuclear medical imaging application, there remains a tremendous unmet need for improved cardiac imaging and functional analysis systems and methods. This need is exemplified by the fact that historically, for 30%-50% of those stricken with coronary artery (occlusive) disease (CAD), the first symptom of the disease is death. This has motivated considerable effort to develop diagnostic methods and apparatus to detect CAD prior to the onset of fatal symptoms and assist in the development and implementation of preventive measures.

Two strategies are presently used to reduce morbidity and mortality from CAD. The first involves screening for modifiable cardiac risk factors, such as hypertension, elevated serum cholesterol, cigarette smoking, physical inactivity, and diet. The second involves early detection of CAD. The principal tests for detecting CAD include resting and exercise ECGs, which can reveal the presence of myocardial infarctions and inducible myocardial ischemia. Tc-99m myocardial perfusion and computed tomography (CT) calcification scoring can provide visual evidence of plaques in the coronary arteries. Thallium-201 scintigraphy, exercise echocardiography, and ambulatory ECG (Holter monitoring) are less commonly used for screening purposes. None of these strategies has produced a solution to the high incidence of death due to undetected CAD. Accordingly, there remains an unsatisfied need for improved cardiac imaging and functional analysis systems and methods for reducing morbidity and mortality from CAD.

SUMMARY OF INVENTION

The following presents a simplified summary of the invention in order to provide a basic understanding of some of its aspects. This summary is not an extensive overview of the invention and is intended neither to identify key or critical elements of the invention nor to delineate its scope. The primary purpose of this summary is to present some concepts of the invention in a simplified form as a prelude to the more detailed description that is presented later.

One aspect of the invention relates to a method of imaging a myocardial infarction in a patient. This method delineates the infarction-produced focal defect in myocardial contractility by imaging the corresponding adjacent phase defect in the cyclic change in radioactivity from a tracer passing through the heart chamber blood. The method produces a phase map of the ventricular blood which shows the location and extent of the myocardial damage caused by the heart attack.

Another aspect of the invention is a method for imaging myocardial infarction in a patient having a bloodstream and a heart having a left ventricle and a right ventricle, including injecting the bloodstream with a bolus having a radioactive tracer, producing a representative cycle for right ventricular bolus passage and a representative cycle for left ventricular bolus passage based on planar coordinates over time of scintillation events of the tracer, and generating a time activity curve based on activity in each segment of the respective representative cycles.

Another aspect of the invention is a method for imaging myocardial infarction in a patient having a bloodstream and a heart having a left ventricle and a right ventricle, including injecting the bloodstream with a bolus having a radioactive tracer, producing a representative cycle for right ventricular bolus passage and a representative cycle for left ventricular bolus passage based on planar coordinates over time of scintillation events of the tracer, and generating a time activity curve based on activity in each segment of the respective representative cycles.

An advantage of the invention is that it utilizes first pass rather than equilibrium pool planar angiography. This results in greatly reduced image distortion due to such factors as respiratory motion and crosstalk. The small changes in myocardial motion due to infarction otherwise can be completely obscured by image distortions inherent in standard equilibrium (MUGA) phase measurements.

Another advantage of the invention is the timing precision (temporal resolution) of the cyclic change in blood tracer is accurate to 0.001 second. Also, data is acquired in list mode rather than in frame mode.

Another advantage of the invention is that it uses a 30 degree right anterior oblique view of the heart which is optimal for visualizing the maximum extent of myocardial wall in profile and the heart valves are nearly perpendicular to the imaging plane. This minimizes the valve distortion of the phase maps of the ventricular blood pool and enhances valve plane delineation by functional imaging.

Another advantage of the invention is that the ventricular phase maps are strictly and accurately limited by the blood pool edges.

Another advantage of the invention is the uniform division of each ventricular cycle into 16 fractions (intervals). Thus, each cycle is divided equally (i.e., divided into the same number of intervals), to a precision of $1/1000$ seconds, regardless of whether the actual time duration of the different cycles are actually equal. This removes any possible distortion that may occur due to different time lengths of cycles. The division of a cycle time into 16 intervals is for convenience. It would be readily apparent to one of ordinary skill in the relevant art to divide the cycles into a different number of intervals, e.g., 32. Compare the present invention with MUGA which divides each cycle into 20-30 millisecond "bins." MUGA's resulting data is distorted because each cycle may be divided into a different number of bins depending on the time length of each such cycle.

Other advantages and novel features of the invention will become apparent from the following detailed description of the invention and the accompanying drawings. The detailed description and drawings provide certain illustrative examples of the invention. These examples are indicative of but a few of the various ways in which the principles of the invention can be employed.

EMBODIMENTS OF THE INVENTION

Figure 1:
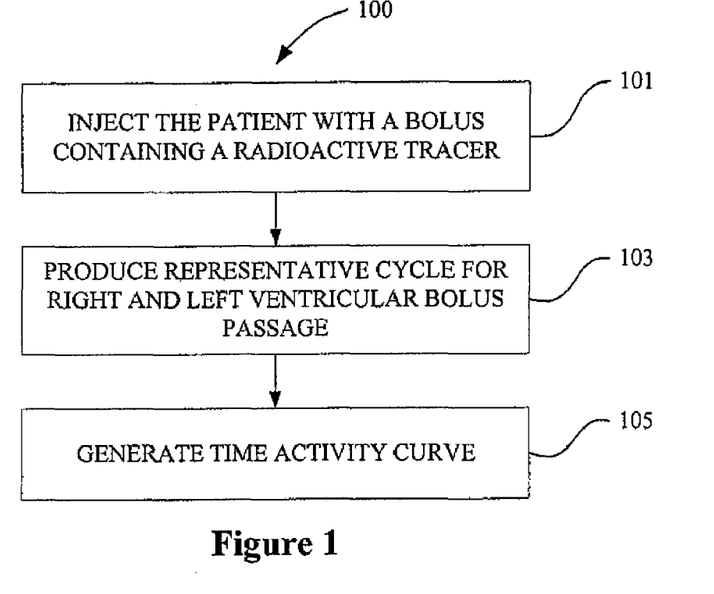
FIG. 1 is a flow chart illustrating a method of imaging a myocardial infarction in accordance with one aspect of the present invention.

FIG. 1 provides a flow chart illustrating a method 100 of imaging a myocaridal infarction in a patient in accordance with one aspect of the present invention. The method involves action 101, injecting a patient with a radioactive bolus, action 103, producing a representative cycle for right ventricular bolus passage and a representative cycle for left ventricular passage, and action 105, generating a time activity curve based on activity in each segment of the respective representative cycles.

Acute myocardial infarction characteristically presents with an acute onset of severe chest pain at rest. The present method 100 is used to delineate the infarction-produced focal defect in myocardial contractility by producing a phase map of the ventricular blood flow through a patient's heart that shows the location and extent of the myocardial damage to the heart. The method 100 thus can inform a health care provider whether a patient's chest pain is due to a myocardial infarction.

Blood flows through the coronary circulation system due to a pressure differential created by the heart. The flow passes first through the major coronary arteries, which have the largest diameters, then through minor coronary arteries, which have smaller diameters, and then through capillaries, which have the smallest diameters. In a healthy patient, the capillaries are the bottleneck of the system and primarily limit the flow rate. For inducible myocardial ischemia to occur, one or more of the largest diameter vessels, the major coronary arteries, must become almost completely occluded.

Acute myocardial infarction (AMI) is the rapid development of myocardial necrosis caused by a critical imbalance between the oxygen supply and demand of the myocardium. This usually results from plaque rupture with thrombus formation in a coronary vessel, resulting in an acute reduction of blood supply to a portion of the myocardium.

The most common cause of AMI is narrowing of the epicardial blood vessels due to atheromatous plaques. Plaque rupture with subsequent exposure of the basement membrane results in platelet aggregation, thrombus formation, fibrin accumulation, hemorrhage into the plaque, and varying degrees of vasospasm. This can result in partial or complete occlusion of the vessel and subsequent myocardial ischemia. Total occlusion of the vessel for more than 4-6 hours results in irreversible myocardial necrosis, but reperfusion within this period can salvage the myocardium and reduce morbidity and mortality.

Action 101 is injecting a patient with a bolus containing a radioactive in a suitable carrier medium. The volume of the bolus is, for example, from about 1 to about 10 cc. The bolus is injected at a suitable point, for example, the antecubital vein of the right or left arm. A suitable radioactive tracer decays to produce gamma particles or alternatively positrons, which rapidly combine with electrons to produce gamma particles. Examples of suitable radioactive tracers include Tc-99m DTPA, I-131 labeled hippuran, I-123, In-111, In-113m, Tl-201, F-18 labeled fluorodeoxyglucose, Cu-62-PTSM, and O-15 labeled water. The half-lives of these tracers vary from a few minutes to a few hours. Dosages are selected with due consideration for patient health and government regulations. For example about 1 to about 20 milliCurie of Tc99m (140 keV) DTPA can be used or about 50 to about 300 microCurie of hippuran labeled with I-131 (360 keV). Higher energy tracers are preferred in that absorption correction is much less important and smaller doses can be used.

The bolus is preferably injected in such a way as to provide a single slug of tracer that circulates through the bloodstream. Although the tracer gradually disperses as it flows through the bloodstream, it is desirable to maintain as tight a dispersion as possible at the time of injection. A fractionated bolus, that is one that is separated into two or more slugs, is preferably avoided.

According to another aspect of the invention, a gamma particle detector is used to observe the shape of the injected bolus upstream of a region of interest. For example, where the region of interest is a left ventricle region, the bolus can be observed as it passes through the thorax. If the bolus shape is fractionated or otherwise unsuitable, the procedure can be aborted and/or later repeated.

Action 103 is producing a representative cycle for right ventricular bolus passage and a representative cycle for left ventricular bolus passage based on planar coordinates over time of scintillation events of the tracer. For example, after a gamma emitting tracer is bolus injected, the planar coordinates of the scintillation events are recorded with millisecond time markers. Data can be acquired for about 20 seconds. The two right ventricular cycles of highest count rate during bolus passage are each divided into time segments that are the same fraction of cycle length. For example, if the first of the two cycles is divided into 16 intervals, each interval would be exactly 1/16th of the total length of that cycle. The second of the two cycles is also then divided into exactly 16 segments that are proportional to the total length of that cycle. These time intervals are fitted with 1/1000th second accuracy. The corresponding 1/16th intervals of the two cycles are added to produce a representative cycle. Similarly, the three highest count rate cycles of the left ventricular bolus passage can be combined to produce a representative cycle.

Figure 2:
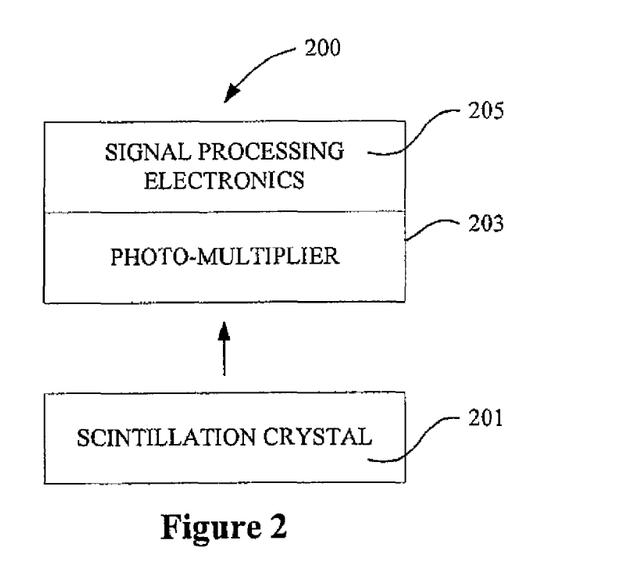
FIG. 2 a high level schematic of a gamma particle detector.

Measuring the time variation in radioactivity involves the use of one or more gamma particle detectors. FIG. 2 provides a high level schematic of an exemplary gamma particle detector 200. Gamma particle detector 200 includes scintillation crystal 201, photo-multiplier 203, and signal processing electronics 205. Gamma particles interact with scintillation crystal 201 to produce flashes of light that are detected by photo-multiplier 203. When photo-multiplier 203 detects a flash of light, it provides a signal to electronics 205. Electronics 205 can include any combination of suitable components, such as scalers, amplifiers, and logic circuits. Scalers are typically employed to provide an output that represents number of detection events per time interval.

Figure 3:
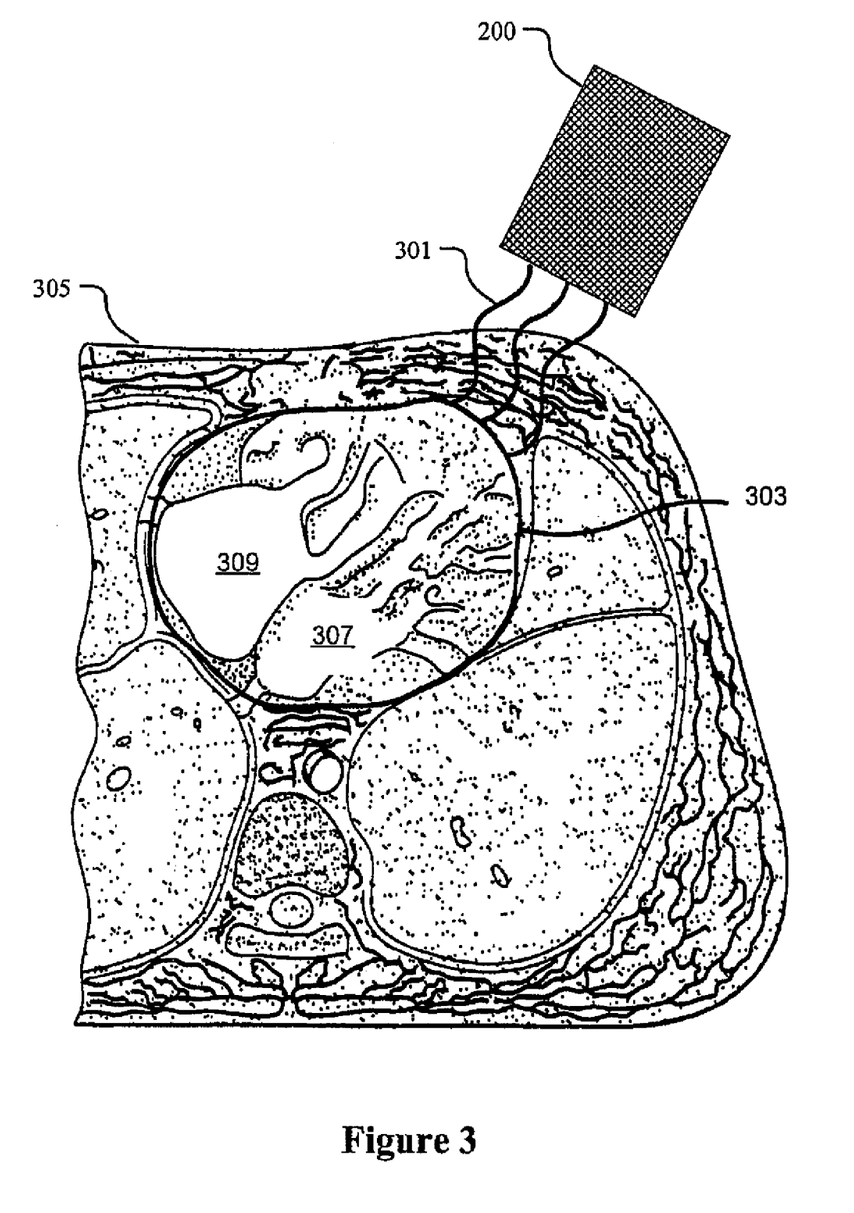
FIG. 3 illustrates, with a view from the feet, a gamma particle detector measuring the time variation in radioactivity from a left ventricle region of a patient.

FIG. 3 illustrate gamma particle detector 200 in use to measure the time variation in radioactivity from a left ventricle region of a heart 303 of patient 305. The left ventricle region substantially includes left ventricle 307 of the heart 303 while substantially excluding the right ventricle 309. Radiation 301, which is a portion of the radiation produced by the radioactive tracer, leaves the heart 303 and reaches gamma particle detector 200. Gamma particle detector 200 provides the number of gamma particles detected per unit time, which is a measure of the amount of radioactive tracer present in the left ventricle region of the heart 303. The count rate of gamma particles in excess of background levels provides the measure of radioactivity from the bolus. This measure varies over time as the bolus passes through the region of interest. Measurements are made over a period that is generally about 30 seconds or less.

The left ventricle region of the patient generally encompasses the left ventricle, although it may include only a portion of the left ventricle. As a practical matter, the left ventricle region also includes portions of the patient outside the left ventricle. The left ventricle region is selected such that the radiation detected is primarily due to radioactive tracer passing through the left ventricle and the coronary circulation system. Radioactive tracer passes through the right heart prior to passing through the left heart. Detection of radioactive tracer passing through the right heart is preferably minimized in action 103.

Scintillation crystal 201 is made with an appropriate scintillation material, for example, NaI(Tl), LSO, GSO, CsI(Tl), YSO, or CsI(Na). The scintillation material is selected to permit detection of gamma photons with energies of at least about 60 keV. Preferably, the thickness permits detection of gamma photons with energies of about 511 keV, whereby gamma photons produced by positron-electron interactions can be detected. For example, crystals of about 2.5 cm thick NaI(Tl), about 2-3 cm thick Gadolinium Oxyorthosilicate (GSO), or about 2 cm thick Luthetium Oxyorthosilicate (LSO) can be used. GSO and LSO scintillators are faster and have higher stopping power for 511 keV photons than NaI(Tl) but are also more expensive and have lower energy resolution for lower energy photons, such as 140 keV from Tc99m.

Figure 4:
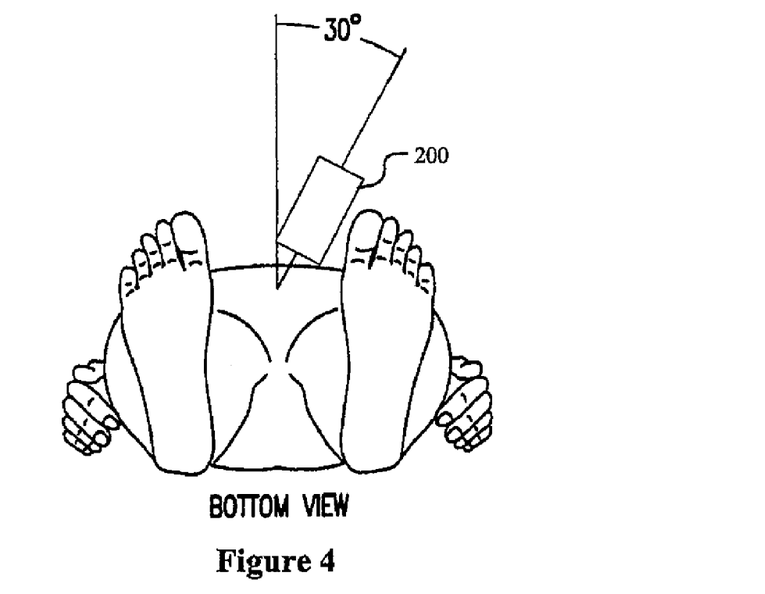
FIG. 4 is a bottom view of a patient illustrating a preferred position for a gamma particle detector in a method of screening patients for an early stage of CAD.
Figure 5:
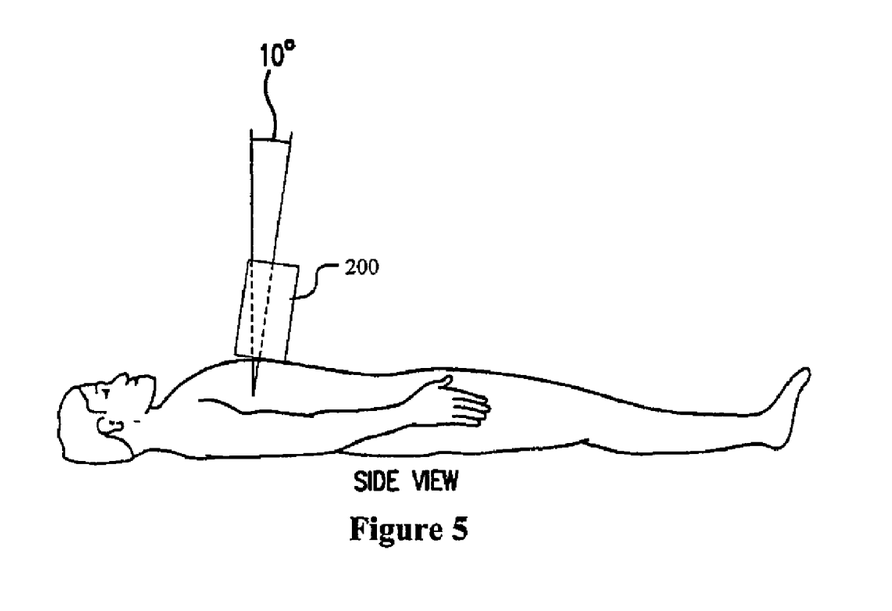
FIG. 5 is a side view of a patient illustrating a preferred position for a gamma particle detector in a method of screening patients for an early stage of CAD.

In some cases, a gamma particle detector can be directed toward the patient's left ventricle using for orientation and guidance external anatomical features, such as the locations of ribs. A preferred position of the detector 200 is approximately 30 degree right anterior oblique and in close proximity to the patient, as illustrated in FIGS. 4 and 5. This generally gives a view perpendicular to the long axis of the cardiac chamber. However, due to anatomical variations that occur among individuals, this is not always the case. Observations of external anatomical features alone do not permit consistent accurate location of the left ventricle.

According to one aspect of the invention, an array of detectors is employed, whereby data can be obtained for an array of locations that is greater than the left ventricle region or other region of interest. The array of locations can be chosen so that there is a high degree of certainty that the left ventricle region is within the array. In this context, an array of detectors includes a plurality of detectors physically arranged to collect data over a contiguous area greater than that observed by any one detector in the array. The data from the detector array can be analyzed to determine a subset of detectors in the array that substantially correspond to the left ventricle region.

Figure 6:
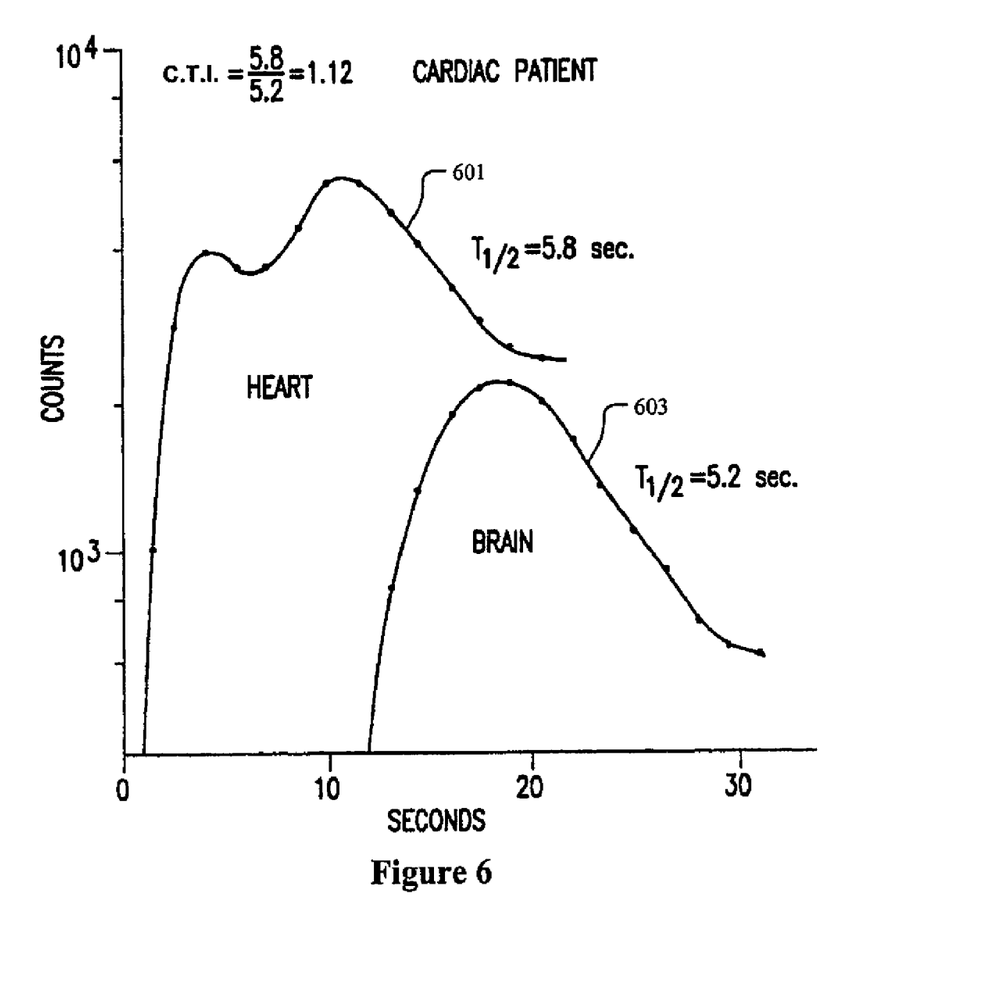
FIG. 6 is a graph show time-activity curves for the heart and brain regions of a cardiac patient.

Detector data corresponding to the left ventricle can be identified from characteristics of the time-activity curve. FIG. 6 illustrates the shape of a time-activity curve 601, which corresponds to a portion of the heart, and time-activity curve 603, which corresponds to the brain. The heart curve 601 has a characteristic double peak structure. The left peak results from flow through the right heart, while the right peak results from flow through the left ventricle.

There are a variety of methods by which time-activity curves corresponding to the left ventricle can be identified. According to one method, the left ventricle time-activity curves are those having a double peak structure and in which the height of the left peak is less than or equal to a certain fraction, about 80% for example, of the height of the right peak. More generally, left ventricle time activity curves can be identified by their functional form. Another method screens the curves according to a learning probabilistic model, such a neural net. Such a model is trained by having an expert manually review a plurality of time activity curves and identifying which do and which do not correspond to the left ventricle.

While the left ventricle region can be taken as that which corresponds to the detector that provides the data most definitively produced from the left ventricle, it is preferred that the left ventricle regions include all the detectors corresponding to the left ventricle. Using all the data increases the signal to noise ratio.

Some clustering or grouping of the detector data often takes place prior to screening for the data corresponding to the left ventricle. For example, if the detector array provides data in a 16×16 square array with 256 elements, the data may be grouped to form a 4.times.4 array with only 16 elements. The grouped elements have greater signal to noise ratio but lower spatial resolution. The optimal grouping can depend on the particular data set, including the location of the left ventricle within the array. Thus it can be desirable to use an iterative algorithm wherein the grouping of the array elements is redefined after a preliminary determination of the left ventricle region.

Figure 7:
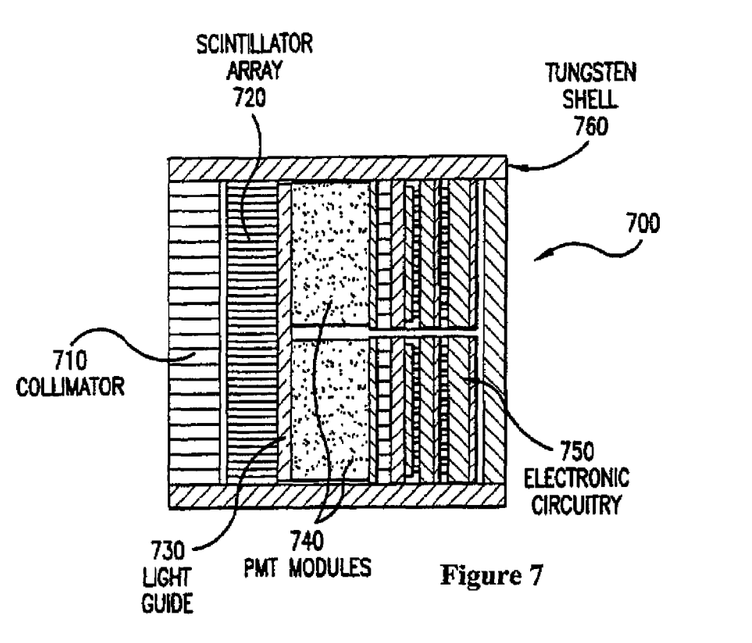
FIG. 7 is an illustration of a gamma particle detector array.

FIG. 7 is a schematic illustration of an exemplary detector array 700. Detector array 700 is also a gamma camera. Detector array 700 includes collimator 710, scintillator array 720, light guides 730, photo-multipliers 740, electronic circuitry 750, and tungsten shell 760. Gamma particles passing through collimator 710 strike scintillator array 720. Scintillator array 720 responds to the gamma particles by producing scintillation light. Light guides 730 guide the scintillation light to photo-multipliers 740. Photo-multipliers 740 produce signals in response to the light that are processed by electronic circuitry 750. Detector array 700 provides count rates for a plurality of spatially segregated positions, the spatial resolution generally being limited by collimator 710.

Scintillator array 720 generally comprises a pixellated scintillation crystal. Alternatively, a scintillator array can be constructed using an array of individual scintillation crystals. The number of elements in the array is selected according to the desired spatial resolution of the detector array 700.

Light guides 730 are employed to guide light from scintillator array 720 to photo-multipliers 740. Light guides 730 can serve to capture light that would otherwise strike between elements of a photo-multiplier array. Generally, light guides 730 are optional.

Photo-multipliers 740 produce signals corresponding to light from the scintillator array 720. The point of origin for the light within scintillator array 720 can be determined using a center of gravity calculation applied to individual signals from photo-multipliers 740. Photo-multipliers can be provided in one-to-one correspondence with scintillation array elements, in which case light guides 730 can be used to guide light from scintillator array elements to corresponding photo-multipliers.

Figure 8:
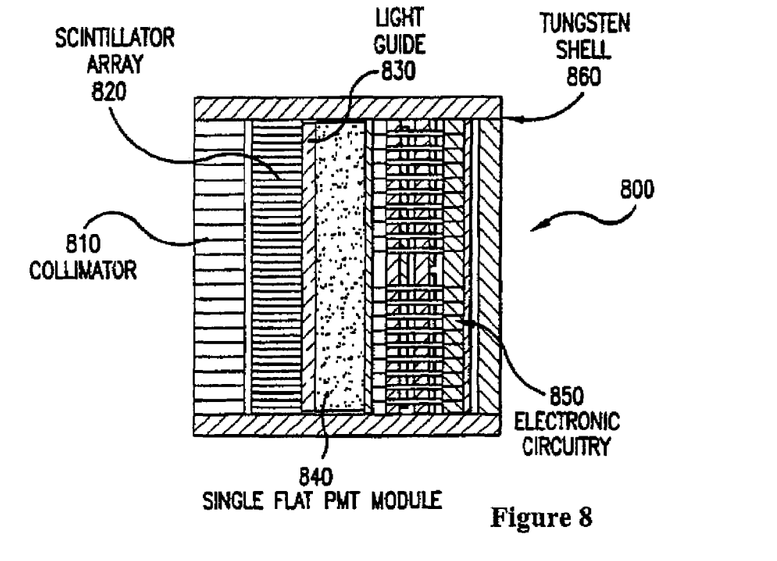
FIG. 8 is an illustration of a gamma particle detector array with a flat position sensitive photo-multiplier tube.

While a detector can employ a plurality of conventional photo-multipliers, the detector can be made substantially more compact by employing position-sensitive photo-multipliers, particularly flat position sensitive photo-multipliers. FIG. 8 illustrates an exemplary detector array 800 employing a flat position-sensitive photo-multiplier 840. In addition to flat position-sensitive photo-multiplier 840, detector array 800 includes collimator 810, scintillator array 820, light guide 830, electronic circuitry 850, and tungsten shell 860.

A position-sensitive photo-multiplier is a photo-multiplier that provides information relating to the location within the photo-multiplier's field of view where light was detected. For example, Hamamatsu Model Nos. R7600-C8, R7600-C12, R7600-M4, and R8520-C12 are suitable for use in the present invention. An array of position-sensitive photo-multipliers can also be employed. For example, a 2.times.2, 4.times.4, 6.times.6, 8.times.6, or 8.times.8 square array. Whenever an array of photo-multipliers is used, it is preferable that the photo-multipliers have a square, hexagonal, or other shape that allows close packing, whereby the array is compact.

Figure 9:
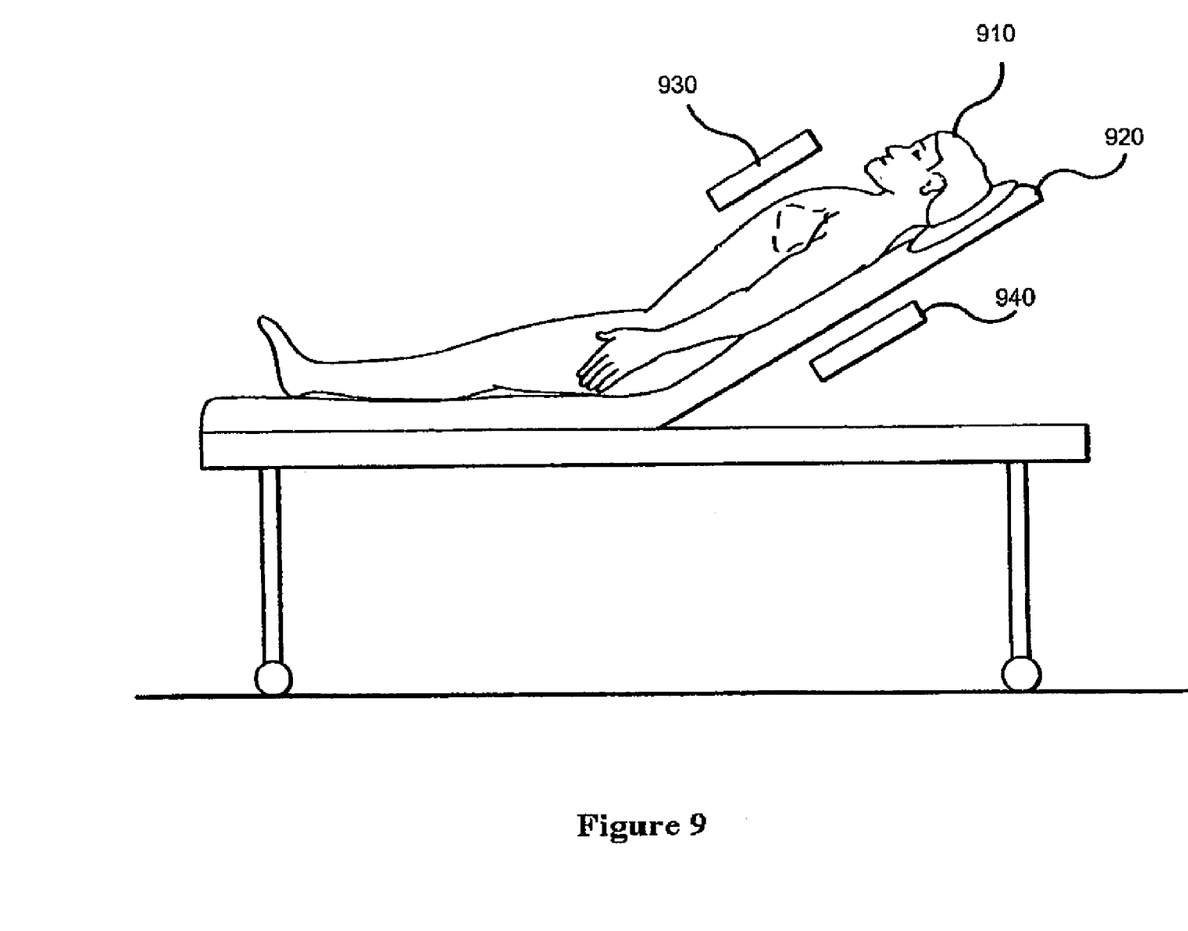
FIG. 9 illustrates the use of two gamma particle detector arrays to detect and locate positron emitters.

Detector arrays 700 and 800 do not necessarily have high spatial resolution. Spatial resolution can be sacrificed in favor of high signal to noise ratio and/or high temporal resolution. In one embodiment, a detector array provides a spatial resolution of about 1 cm or larger.

Where the radioactive tracer produces positrons, spatial resolution can be achieved without the use of collimators. When positrons combine with electrons, two gamma particles are emitted in opposite directions. By detecting both gamma particles using two gamma particle detector arrays located opposite one another, and by comparing the locations within the arrays where the gamma particles are detected, points of origin for the gamma particles can be determined. FIG. 9 illustrates a patient 910, lying on a table 920, with gamma particle detector arrays 930 and 940 facing each other and both oriented towards a left ventricle region of the patient 910, whereby positrons in the left ventricle region can be detected. Alternatively, a single detector array can be used to detect positrons, although a high-energy collimator, such as one made of tungsten, is required in order to obtain spatial resolution.

According to another aspect of the invention, a gamma particle detector is positioned for use in method 100 according to the location of a left ventricle region as determined by a suitable detection method. In this aspect of the invention, a single detector is often used instead of a detector array. The location of the left ventricle can be determined by any suitable technique, including for example ultrasound, MRI, x-ray, computed tomography, planar nuclear medicine, positron emission spectroscopy, single photon emission computed tomography, or a second radioactive tracer. For example, a small amount of Tl-201 (on the order of 50 microCurie) can be injected and the left ventricle region located based on a detector position that provides the maximum count rate. The injection used to locate the left ventricle region is generally performed 5-10 minutes before the main bolus injection.

Regardless of how the left ventricle region is located, or whether a detector array is used, method 100 is preferably carried out with one or more high temporal resolution gamma particle detectors. In one embodiment of the invention, the gamma particle detector has a temporal resolution of about 0.1 seconds or better. In another embodiment, the gamma particle detector has a temporal resolution of about 0.03 seconds or better. In a further embodiment, the gamma particle detector has a temporal resolution of about 0.01 seconds or better.

Preferably, the gamma particle detectors realize a high signal to noise ratio. The magnitude of the signal is limited in part by the amount of radioactive tracer contained in the bolus. In one embodiment, one or more detectors have a signal to noise ratio giving a measurement error of less than about 10%. In another embodiment, the measurement error is less than about 3%. In a further embodiment, the measurement error is less than about 1%. The detector head is preferably encased with ¼-½ inch thick tungsten shielding to reduce background noise.

Where a detector array is employed, the measurement error can be reduced at the cost of spatial resolution. At lower spatial resolution, each separately observed spatial region within the patient produces a sufficient number of detected radiation events within a measurement interval to produce a measurement with the required statistical accuracy. For example, if the required temporal resolution is 0.01 seconds and 1000 events per interval are required to achieve the desired signal to noise ratio, the detected event rate for a single detector must reach about 100 kHz.

The gamma particle detector, or detector array, used to obtain measurements from the region of interest is preferably portable and preferably dedicated to heart diagnosis. A unit dedicated to heart diagnosis generally takes measurements over an area about the size of the heart. In one embodiment, the detector or array takes measurements over an area of about 40 cm.sup.2 or less. In another embodiment, the detector or array takes measurements over an area of about 20 cm.sup.2 or less. In a further embodiment, the detector or array takes measurements over an area of about 10 $cm^2$ or less. The required data can generally be obtained in less than about 30 seconds, preferably less than about 15 seconds. Where data is sought while the patient is under stress, the short time required significantly reduces the burden on the patient as compared to other methods.

Action 105 is generating a time activity curve based on activity in each segment of the respective representative cycles from action 103. The activity in each segment of the representative cycles produces a time activity curve which is actually the volume curve of each chamber. These functions can be smoothed with a Fourier filter which preserves the curve nadirs. The spatial distribution of counts generates an image of each interval of the cardiac cycle. For each pixel of the image, the phase and amplitude of the first harmonic of the respective time and activity curve can be determined. The first harmonic is a perfect sinusoidal oscillation and is a symmetric approximation of the time activity curve. The latter is a periodic function without discontinuities. The position of the sinusoid's nadir, i.e., its phase, is very strongly influenced by the nadir of the time activity curve. The temporal location of the nadirs is far more accurate using this method 100 than with prior techniques because of greater temporal resolution. The result of this processing is the original data contained in 16 or more images is reduced to only two images. Each picture element of these images represents, respectively, the amplitude and phase shift values of the sinusoidal curve obtained from the count rate changes that occur during the cardiac cycle in each pixel.

The phase data is presented as planar images of the right and left ventricular blood pools. In a normal heart, myocardial contractility is synchronous. The resultant cyclic count rate changes in the blood pool pixels are all in phase with one another. If the phase values of each picture element are coded as a color or shade of gray, then the phase map of the normal ventricle is of uniform color or shade of gray. When a segment of heart muscle is damaged, its contraction ceases or lags behind the normal surrounding myocardium. This produces a phase shift in the adjacent blood pool pixels which can be displayed as a focal change of color or gray scale. In addition to the phase map, a histogram of the phase values of all of the pixels can be presented which quantifies the extent of myocardial damage responsible for the phase defect.

Another aspect of the invention relates to a high temporal resolution gamma particle detector array, which is a gamma camera. The camera can be used for first pass imaging, positron imaging, quantitative myocardial perfusion measurements, planar hot spot imaging, and planar, gated, non-gated, and multi-gated pooled blood imaging. These images can be used for such purposes as measuring regional ventricular wall motion, measuring left and right ventricular ejection fractions, measuring blood flow in the myocardium, measuring regional contractivity, measuring synchrony, detecting infarct sites and abnormalities of conduction, and left to right shunt quantification.

Figure 10:
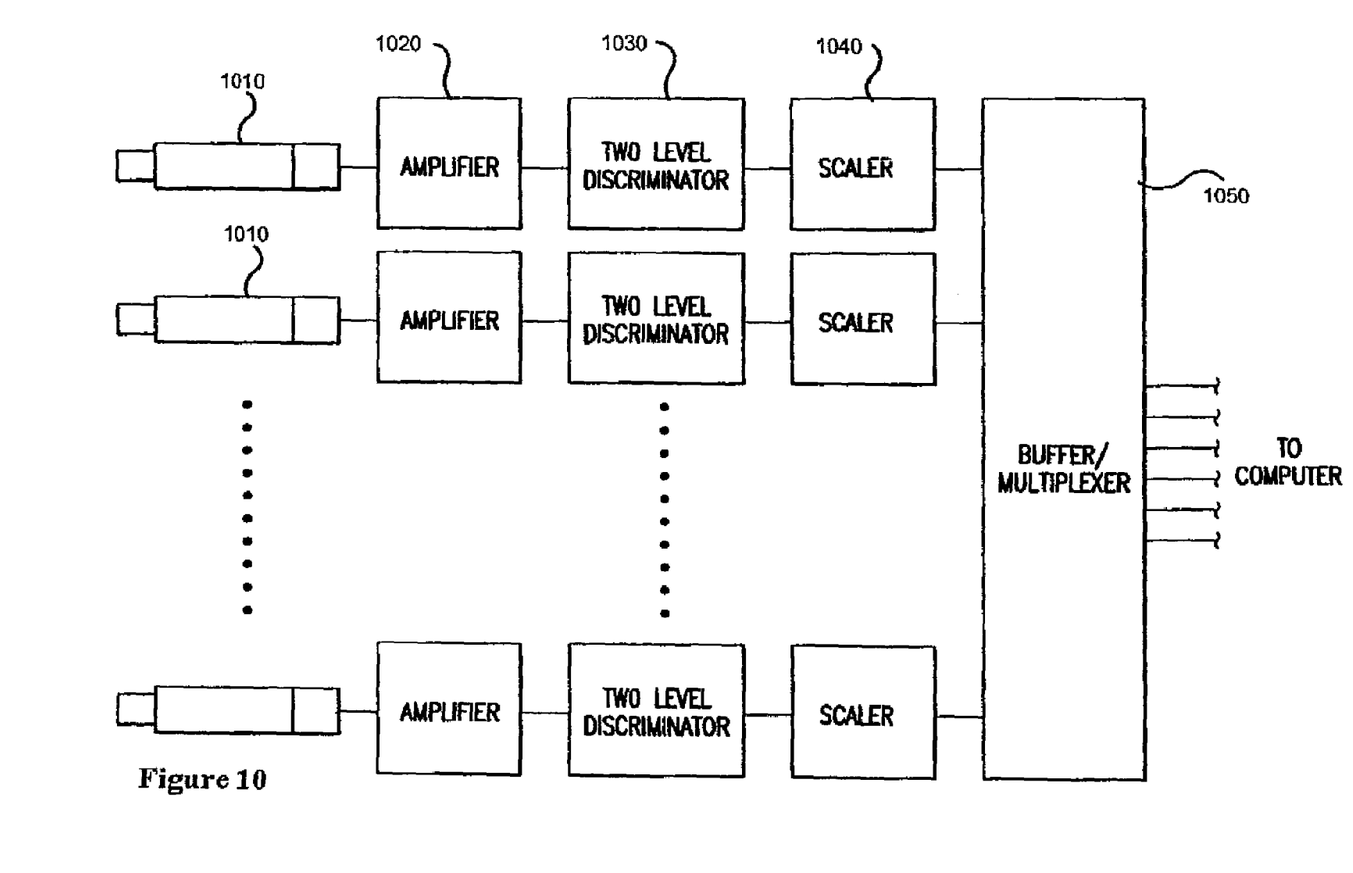
FIG. 10 is a schematic illustration of electronics for parallel processing of photo-multiplier data according to one aspect of the present invention.

High temporal resolution can be achieved, in part, by configuring the electronic circuitry for parallel processing of data from the photo-multiplier or photo-multiplier array. FIG. 10 illustrates one electronic circuitry configuration for achieving such parallel processing. In FIG. 10, each of a plurality of photo-multiplier tubes 1010 is coupled to a corresponding amplifier 1020. The amplified signals are provided to corresponding two level discriminators 1030, which distinguish those signals that have sufficient energy to correspond to the radioactive tracer in use. The output of the two level discriminators 1030 is fed to scalers 1040, which count the number of events and periodically supply output to buffer/multiplexer 1050. Buffer/multiplexer 1050 combines the count rates provided by the various scalers into a single output stream that can be provided to a computer.

Figure 11:
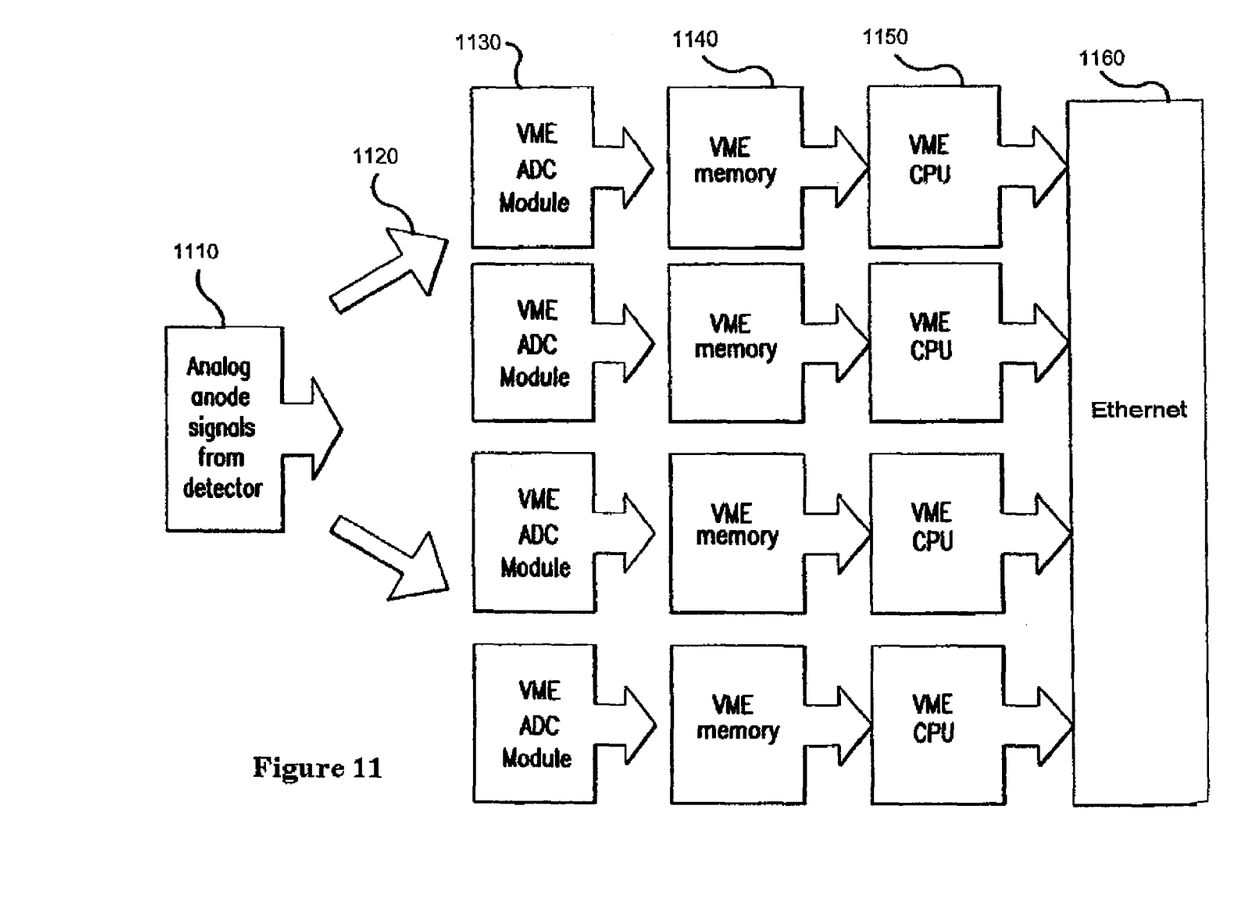
FIG. 11 is a schematic illustration of electronics for parallel processing of photo-multiplier data according to another aspect of the present invention.

Some additional options for configuring the electronic circuitry for parallel processing are illustrated in FIG. 11. FIG. 11 shows the signals coming from various anodes 1110 of one or more photo-multipliers. There does not need to be a one-to-one correspondence between parallel channels 1120 and either anodes or photo-multipliers. Rather, the signal processing can be divided in any suitable fashion. The anode signals are supplied through channels 1120 to VME analog-to-digital converter modules 1130. The digital data is accumulated in VME memories 1140 and processed by CPUs 1150. The data can then be shared across a network, such as ethernet 1160.

A gamma camera of the present invention can be made compact and portable. Such a camera can be positioned in close proximity to the heart from several different directions, which facilitates first-pass analysis and measuring ejection fractions from both left and right ventricles. A compact camera is particularly useful in intensive care units, where space is at a premium. The camera can be provided with a support gantry/harness to provide co-registration with the patient's body.

In imaging the heart, it is often desirable to compensate for patient motion. This is particularly true when heart function is being analyzed while the patient is active. One approach to compensating for patient motion is to place a radiation source on the patient's body as a point of reference. For example, an Am-241 source can be fixed to the patient's chest. The location of the source can be used to correct for patient motion in a plane perpendicular to the gamma camera. The reference source can be distinguished from the tracer, if desired, using dual energy windows.

Figure 12:
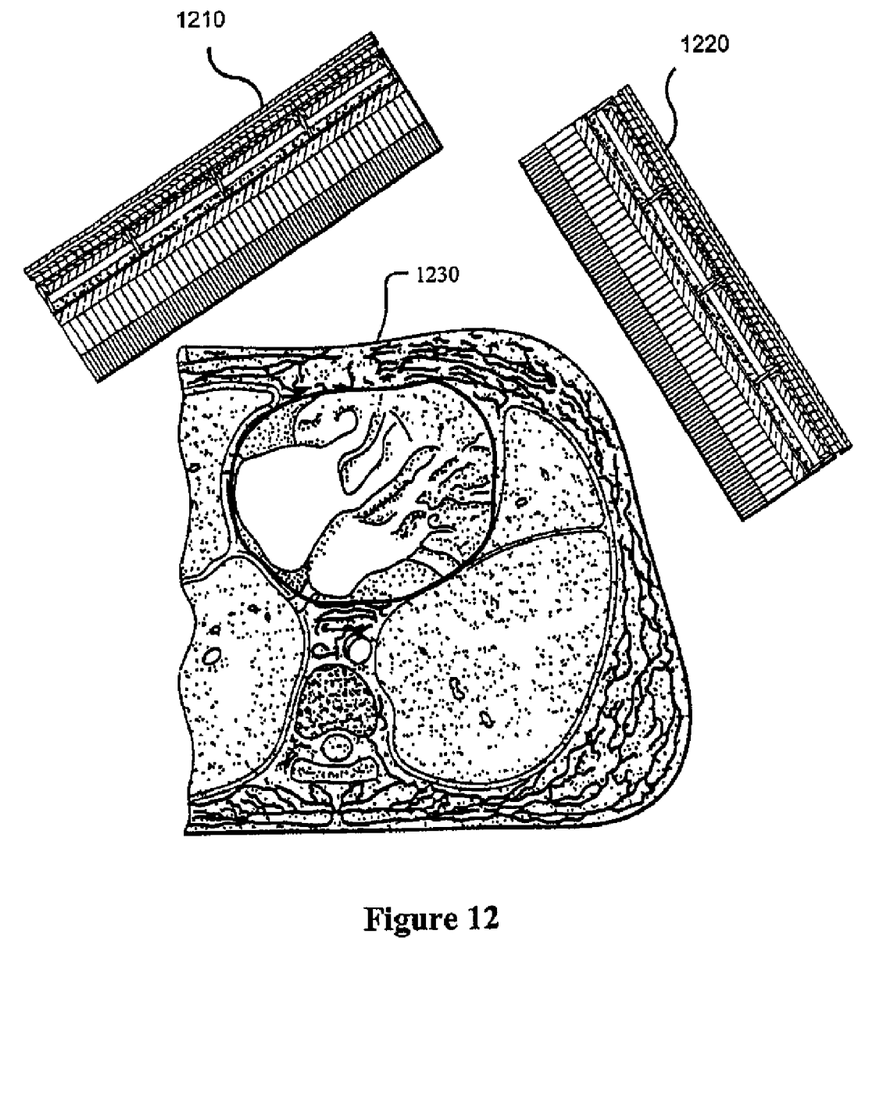
FIG. 12 is an illustration of a system that employs two gamma particle detectors.

According to a further aspect of the invention, a second camera is placed at an approximately right angle to the first camera head, whereby the system can compensate for patient motion in any direction. FIG. 12 illustrates two gamma cameras, 1210 and 1220, arranged in such a manner and oriented toward the left ventricle region of a patient's body 1230. In addition to facilitating compensation for patient motion, a second camera also allows all edges of the ventricular blood pool to be viewed simultaneously. These include the antero-lateral, apical, posterior, septal, and posterior-lateral walls. The second view also increases the accuracy of the diastolic chamber volume calculation and provides information that can be used in correcting for heart movement in first pass test procedures.

In one embodiment of the invention, cardiology data can be collected from a patient through the use of a commercially available digital, gamma camera. The camera is used in the conventional way in that a gamma emitting bolus is injected into the patient's blood stream and then the camera is used to take numerous pictures of the blood being contracted by the patient's heart as the bolus first flows through the patient. Data preferably is acquired for about 20 seconds. The cardiology data, i.e., the contraction of the blood, is captured during the first pass of the bolus through a patient's heart.

Software accomplishing the desired objectives of the method 100 may be written using the Visual C++ programming language or any comparable programming language. It would be readily apparent for one of ordinary skill in the relevant art to design and implement the described software and system of the present invention. Data may be input either manually or serially from the gamma camera.

Hardware, e.g., a computer system or laptop, running the software of the present invention can be linked to a gamma camera via a standard port connection capable of handling a data transmission rate of about 200 MegaHertz. However, similar means of connecting data collection devices to computer hardware and/or storage devices may alternatively be used. For example, in an alternative embodiment, the gamma camera is not connected to the computer system of the present invention, but rather, the camera transmits its output data to a laptop, or comparable computer system, via a wireless connection. In this embodiment, one computer system can be accessed remotely by a plurality of digital, gamma cameras. Such wireless connections are well known in the relevant art such that it would be readily apparent to one of ordinary skill in the relevant art to implement the present invention using wireless technology.

The retrieval and storage of a patient's cardiology data includes the ability to generate real-time, easy to read reports of such cardiology data, including a report on the size and location of a myocardial infarction; relates current cardiology data to historical data; relates cardiology data to treatment history; and allows a health care worker to study relationships between the cardiology data and other related environmental or health factors.

This invention may be used in any clinical setting where information needs to be captured in a database and immediately viewed, printed, stored, and associated with other data parameters such as medical history, treatment regime, and other environmental or medical information.

An embodiment of the present invention can combine off-the-shelf hardware components through software and a conventional computer system. A sample computer system can include one or more processors that are connected to a communication bus. The computer system can also include a main memory, preferably random access memory (RAM), and a secondary memory. The secondary memory includes, for example, a hard disk drive and/or a removable storage drive, representing a floppy disk drive, a magnetic tape drive, a compact disk drive, a program cartridge and cartridge interface (such as that found in video game devices), a removable memory chip (such as EPROM, or PROM), etc. which is read by and written to by a removable storage unit. The removable storage unit, also called a program storage device or a computer program product, represents a floppy disk, magnetic tape, compact disk, etc. As will be appreciated, the removable storage unit includes a computer usable storage medium having stored therein computer software and/or data. The removable storage drive reads from and/or writes to a removable storage unit in a well known manner.

The computer system may also include other similar means for allowing computer programs or other instructions to be loaded. Such means can include, for example, a communications interface. Communications interface allows software and data to be transferred between the computer system and external devices. Examples of communications interface can include a modem, a network interface (such as an Ethernet card), a communications port, etc. Software and data transferred via communications interface are in the form of signals which can be electronic, electromagnetic, optical or other signals capable of being received by communications interface.

In this document, the term "computer program product" is used to generally refer to removable storage unit, a hard disk installed in hard disk drive, and signals transferred via communications interface. These computer program products are means for providing software of the present invention to a computer system.

In an embodiment where the invention is implemented using software, the software may be stored in main memory, or in a computer program product and loaded into computer system using removable storage drive, hard disk drive, or communications interface. The software, when executed by the processor(s) of the computer system, causes the processor(s) to perform the functions of the invention as described herein.

In another embodiment, the invention is implemented primarily in hardware using, for example, a hardware state machine. Implementation of the hardware state machine so as to perform the functions described herein will be apparent to persons skilled in the relevant arts.

The preferred embodiment of the present invention is also directed to a computer system including a display device and one or more input peripherals. The display device represents a computer screen or monitor on which a graphical user interface, including a window environment, may be displayed. The input peripherals include, for example, a keyboard, a mouse, a light pen, a pressure-sensitive screen, etc., which provide a user with the capability of entering input to the computer system.

The operating system of the computer system of the present invention is directed to a windows environment. Alternatively, a command line interface may be used. The present invention is described in terms these operating systems for convenience purpose only. It would be readily apparent that any comparable operating system could be used.

The preferred computer system is a laptop system, but the present invention also can be developed on a personal or mainframe computer. The present invention also is described in terms of a computer system having a single processor for convenience purposes only. It would be readily apparent, however, to one skilled in the relevant arts to use a computer system having multiple processors to execute the present invention in parallel. There are no memory requirements for developing and executing the present invention. However, the computer system achieves better performance with more main memory and secondary memory.

In one embodiment, the resulting display shown to the health care provider is a planar representation of the blood being contracted in the ventricles of a patient's heart. The preferred display is either 64×64 or 128×128 pixal display, but this is for convenience. The normal contraction of the blood in the patient's heart is shown as a uniform color, whereas the portion of the blood in proximity to the damaged tissue, i.e., the infarction, is displayed as a second color, e.g., red. Thus, the health care provider easily and rapidly identifies the size and location of the infarction in the patient's heart due to the improper contraction of the blood. In addition, the present invention may employ the use of two or more colors and/or other warnings if certain conditions are detected. For example, different areas of infarction, or different degrees/levels of infarction, may be color-coded, e.g., red indicated a high-risk area or trigger an appropriate alarm.

While the present invention is illustrated with particular examples, other system and methods have been described and are within the scope of the hereto appended claims. The invention and the claims are to be construed as including modifications, alterations, and equivalents that will occur to those of ordinary skill in the art upon reading and understanding this specification.

What is claimed is:

1. A method for detecting myocardial infarction in a patient having a bloodstream and a heart having a left ventricle and a right ventricle, comprising:

injecting the bloodstream with a bolus comprising a radioactive tracer that passes through the heart, wherein said bolus maintains a high concentration of said radioactive tracer relative to the bloodstream prior to said bolus injection as said bolus passes in the bloodstream through the right ventricle and the left ventricle of the heart such that said bolus passes through the heart in the bloodstream in a contiguous form;

obtaining planar coordinates of scintillation events as right images of the right ventricle during a first pass of said bolus in the bloodstream through the right ventricle wherein said bolus maintains a substantially uniform distribution of said high concentration of radioactive tracer in the blood stream in the right ventricle;

obtaining planar coordinates of scintillation events as left images of the left ventricle during a first pass of said bolus in the bloodstream through the left ventricle, wherein said bolus maintains a substantially uniform distribution of said high concentration of radioactive tracer in the blood stream of the left ventricle;

producing a right representative cycle of the right ventricle based on said right images and a left representative cycle of the left ventricle based on said left images;

generating a left ventricular phase map and a right ventricular phase map based on said left representative cycle and said right representative cycle respectively; and assessing damage to the heart based on phase shift changes in said left ventricular phase map or said right ventricular phase map.

2. The method of claim 1, wherein said right images are associated into a plurality of heart cycles, and said right representative cycle of the right ventricle is produced by taking two cycles of highest count rate selected from said plurality of heart cycles, and dividing each of said two cycles into time intervals that are the same fraction of cycle length and adding the corresponding time intervals of said two cycles.

3. The method of claim 2, wherein said first cycle of said two cycles has a first cycle time duration, and said second cycle of said two cycles has a second time duration.

4. The method of claim 3, wherein said first cycle time duration is not equal to said second cycle time duration.

5. The method of claim 1, wherein said left images are associated into a plurality of heart cycles, and said left representative cycle of the left ventricle is produced by taking three cycles of highest count rate selected from said plurality of heart cycles, and dividing each of said three cycles into time intervals that are the same fraction of cycle length and adding the corresponding time intervals of said three cycles.

6. The method of claim 5, wherein said first cycle of said three cycles has a first cycle time duration, and said second cycle of said three cycles has a second cycle time duration, and said third cycle of said three cycles has a third cycle time duration.

7. The method of claim 6, wherein said first cycle time duration, said second cycle time duration, and said third cycle time duration are not equal to each other.

8. The method of claim 1, wherein said right images and said left images are obtained with one or more gamma particle detectors comprising a scintillator array and one or more photomultipliers.

9. The method of claim 8, wherein said right images and said left images are obtained with one or more position-sensitive photo-multipliers.

10. The method of claim 8, wherein said right images and said left images are obtained with electronics that process output from the one or more photo-multipliers in parallel.

11. The method of claim 1, wherein a time-sensitive analysis of the bloodstream through the heart is performed by analyzing said right images to measure the frequency of said scintillation events of said right images and by analyzing said left images to measure the frequency of said scintillation events of said left images.

12. The method of claim 1, further comprising generating a time activity curve based on said right images and said left images wherein said time activity curve is a volume curve of said right ventricle and said left ventricle of the heart.

13. A method for detecting myocardial infarction in a patient having a bloodstream and a heart having a left ventricle and a right ventricle, comprising:
   injecting the bloodstream with a bolus comprising a radioactive tracer that passes through the heart, wherein said bolus maintains a high concentration of said radioactive tracer relative to the bloodstream prior to said bolus injection as said bolus passes in the bloodstream through the right ventricle and the left ventricle of the heart such that said bolus passes through the heart in the bloodstream in a contiguous form;
   obtaining planar coordinates of scintillation events as right images of the right ventricle during a first pass of said bolus in the bloodstream through the right ventricle wherein said bolus maintains a substantially uniform distribution of said high concentration of radioactive tracer in the bloodstream in the right ventricle;
   obtaining planar coordinates of scintillation events as left images of the left ventricle during a first pass of said bolus in the bloodstream through the left ventricle wherein said bolus maintains a substantially uniform distribution of said high concentration of radioactive tracer in the blood stream of the left ventricle;
   producing a right representative cycle of the right ventricle based on said right images, wherein said right images are associated into a plurality of heart cycles and said right representative cycle of the right ventricle is produced by taking two cycles of highest count rate selected from said plurality of heart cycles and dividing each of said two cycles into time intervals that are the same fraction of cycle length and adding the corresponding time intervals of said two cycles, wherein a first cycle of said two cycles of said right images has a first cycle time duration and a second cycle of said two cycles of said right images has a second time duration, and said first cycle time duration is not equal to said second cycle time duration;
   producing a left representative cycle of the left ventricle based on said left images; wherein said left images are associated into a plurality of heart cycles, and said left representative cycle of the left ventricle is produced by taking three cycles of highest count rate selected from said plurality of heart cycles and dividing each of said three cycles into time intervals that are the same fraction of cycle length and adding the corresponding time intervals of said three cycles, wherein a first cycle of said three cycles of said left images has a first cycle time duration, and a second cycle of said three cycles of said left images has a second cycle time duration and a third cycle of said three cycles of said left images has a third cycle time duration, and said first cycle time duration, said second cycle time duration, and said third cycle time duration are not equal to each other;
   generating a left ventricular phase map and a right ventricular phase map based on said left representative cycle and said right representative cycle respectively; and
   assessing damage to the heart based on phase shift changes in said left ventricular phase map or said right ventricular phase map.

14. The method of claim 13, wherein said right images and said left images are obtained with one or more gamma particle detectors comprising a scintillator array and one or more photomultipliers.

15. The method of claim 14, wherein said right images and said left images are obtained with one or more position-sensitive photo-multipliers.

16. The method of claim 14, wherein said right images and said left images are obtained with electronics that process output from the one or more photo-multipliers in parallel.

17. The method of claim 13, further comprising performing a time-sensitive analysis of the bloodstream through the heart by analyzing said right images to measure the frequency of said scintillation events of said right images and by analyzing said left images to measure the frequency of said scintillation events of said left images.

18. The method of claim 13, further comprising segmenting said left representative cycle and said right representative cycle into at least sixteen segments of equal duration prior to generating said left ventricular phase map and said right ventricular phase map.

19. The method of claim 13, further comprising constructing a histogram of said phase shift changes which quantifies the myocardial infarction.

20. The method of claim 13, further comprising generating a time activity curve based on said right images and said left images wherein said time activity curve is a volume curve of said right ventricle and said left ventricle of the heart.

* * * * *